United States Patent
Sarradon

(10) Patent No.: US 10,251,660 B2
(45) Date of Patent: Apr. 9, 2019

(54) SURGICAL FORCEPS FOR PHLEBOTOMY

(71) Applicant: Pierre Sarradon, Toulon (FR)

(72) Inventor: Pierre Sarradon, Toulon (FR)

( * ) Notice: Subject to any disclaimer, the term of this patent is extended or adjusted under 35 U.S.C. 154(b) by 177 days.

(21) Appl. No.: 15/340,802

(22) Filed: Nov. 1, 2016

(65) Prior Publication Data

US 2017/0042559 A1 Feb. 16, 2017

Related U.S. Application Data

(62) Division of application No. 13/699,317, filed as application No. PCT/IB2011/052208 on May 20, 2011.

(30) Foreign Application Priority Data

May 21, 2010 (FR) ...................................... 10 02161

(51) Int. Cl.
  *A61B 17/29* (2006.01)
  *A61B 17/00* (2006.01)
  *A61B 17/32* (2006.01)

(52) U.S. Cl.
  CPC ........ *A61B 17/29* (2013.01); *A61B 17/00008* (2013.01); *A61B 17/2909* (2013.01); *A61B 2017/00738* (2013.01); *A61B 2017/2911* (2013.01); *A61B 2017/2912* (2013.01); *A61B 2017/2926* (2013.01); *A61B 2017/320064* (2013.01)

(58) Field of Classification Search
  CPC .............. A61B 17/00008; A61B 17/29; A61B 2017/00738; A61B 2017/291; A61B 2017/2911; A61B 2017/2926
  See application file for complete search history.

(56) References Cited

U.S. PATENT DOCUMENTS

| | | | |
|---|---|---|---|
| 2,618,268 | A | 11/1952 | English |
| 5,170,800 | A | 12/1992 | Smith |
| 5,234,460 | A | 8/1993 | Stouder, Jr. |
| 5,476,099 | A | 12/1995 | Robinson |
| 5,752,972 | A | 5/1998 | Hoogeboom |
| 5,817,128 | A | 10/1998 | Storz |

(Continued)

FOREIGN PATENT DOCUMENTS

| | | |
|---|---|---|
| JP | 30-7692 | 10/1930 |
| JP | 61-196720 U | 12/1986 |

(Continued)

OTHER PUBLICATIONS

"Notification of Reasons for Refusal" issued by Japanese Patent Office for corresponding Japanese application 2013-510719 dated Oct. 23, 2013 with English translation.

*Primary Examiner* — Robert Lynch
(74) *Attorney, Agent, or Firm* — Haug Partners LLP

(57) ABSTRACT

Surgical forceps for removing varicose veins with surgical forceps and related methods are provided. The surgical forceps comprise an elongate tubular sheath, two jaws mounted movably relative to each other around a pivot axis at a distal end of the tubular sheath, two maneuvering branches each having a ring for the insertion of a finger, and a linkage for transmitting the movement of the maneuvering branches to the jaws. The method comprises inserting a finger in each ring, introducing the surgical forceps into a patient's skin, and moving the maneuvering branches towards one another to move the jaws to a gripping position to grip the varicose veins.

10 Claims, 3 Drawing Sheets

(56) References Cited

U.S. PATENT DOCUMENTS

| | | | |
|---|---|---|---|
| D710,006 S | 7/2014 | John | |
| 2004/0260198 A1 | 12/2004 | Rothberg | |
| 2006/0079933 A1 | 4/2006 | Hushka et al. | |
| 2008/0046001 A1 | 2/2008 | Renger et al. | |

FOREIGN PATENT DOCUMENTS

| | | |
|---|---|---|
| JP | 05-031120 A | 2/1993 |
| JP | 06-296618 A | 10/1994 |
| JP | 8-507714 A | 8/1996 |
| JP | 2004-501715 A | 1/2004 |
| WO | WO 94/21177 A | 9/1994 |
| WO | WO 02/02019 A | 1/2002 |

SURGICAL FORCEPS FOR PHLEBOTOMY

This application is a Division of application Ser. No. 13/699,317 filed Nov. 21, 2012, which is a 371 of PCT/IB2011/052208 filed on May 20, 2011, published on Nov. 24, 2011 under publication number WO 2011/145078 A, which claims priority benefits to French Patent Application 10/02161 filed May 21, 2010, the entire disclosure of which is incorporated herein by reference.

TECHNICAL FIELD OF THE INVENTION

The invention relates to the field of surgical instruments, and in particular the instruments used manually by a practitioner to grasp body tissues.

The invention more particularly relates to a surgical phlebectomy forceps.

BACKGROUND OF THE INVENTION

A phlebectomy is a surgical operation, primarily affecting the lower limbs, which consists of removing segments of varicose veins, said varicose veins being unattractive, painful, and accompanied by an alteration in the circulatory condition which carries a risk of complications.

To allow this removal, the surgeon makes an incision in the patient's skin. He then grasps the vein using a hook known as a "Muller hook," then removes it using "Halsted" or equivalent forceps, inserted into the incision.

However, the use of this type of forceps has the drawback of requiring a relatively large incision, i.e. at least 4 to 5 mm. In fact, the width of the jaws, and particularly the branches, requires a large incision. In particular, the spacing of the branches when the forceps is opened is relatively significant and increases the necessary size of the incisions.

Furthermore, the larger the radius of action of the forceps, the larger the space between the branches. Thus, when the segments of vein to be removed are at a significant distance from the incision, the practitioner must use a forceps with a significant length to make a number of incisions so as to limit the distances between the incisions and the vein segments to be removed and, as a result, the width of the incisions.

Furthermore, these forceps are not very ergonomic. On the one hand, they do not allow sufficient gripping of the vein segments, such that the practitioner is sometimes several attempts by the practitioner are sometimes necessary to remove them. On the other hand, the manipulation of the handling branches near the patient's skin is not easy.

BRIEF DESCRIPTION OF THE INVENTION

The invention aims to resolve these problems by proposing an ergonomic surgical phlebectomy forceps making it possible to decrease the size and number of incisions necessary to remove all of the varicose veins.

To that end, and according to a first aspect, the invention proposes a surgical forceps for removing varicose veins including:
- a body with an articulation plate and an elongate tubular sheath;
- two maneuvering branches mounted on the articulation plate and movable relative to each other between an open position and a closed position, each of these branches having a ring for the insertion of a finger;
- a gripper mounted at the distal end of the tubular sheath and having two jaws mounted movably relative to each other around an axis A between an open position and a gripping position, the inner faces of said jaws being toothed in order to hold the varicose veins; and
- means for transmitting the movement of the maneuvering branches to the jaws, via the tubular sheath, said means being designed to move the jaws to their gripping position when the maneuvering branches are closed together.

Thus, when the forceps is positioned in its position to remove the vein, it is the tubular sheath that is positioned at the incision. However, the sheath has a limited section which also does not vary as a function of the position of the maneuvering branches or the jaws. In this way, the section of the tubular sheath being limited, the width of the incision may be limited.

Furthermore, the presence of a device for transmitting the movement of the maneuvering branches to the jaws, through the sheath, makes it possible to increase the radius of action of the forceps without increasing the width of the incision. The forceps according to the invention then makes it possible to remove veins under the same conditions, whether they are close to or far away from the incision. Consequently, the number of incisions made during an operation may be significantly decreased.

Advantageously, the rings are spaced apart by a distance of at least 1 cm relative to a working plane, orthogonal to the axis A, in which the jaws extend. This embodiment makes it possible to facilitate maneuvering of the forceps, as the rings are thus spaced away from the patient so as to form a free space between the patient and the maneuvering rings.

Advantageously, the rings extend in a maneuvering plane inclined by an angle greater than 10° relative to the working plane and, preferably, inclined by an angle comprised between 20 and 30° relative to the working plane.

Advantageously, the length of the tubular sheath is comprised between 10 and 25 cm. Preferably, the tubular sheath has a section smaller than or equal to 3 mm. In this way, the tubular forceps according to the invention makes it possible to remove veins situated more than 25 cm from the incision without requiring an incision having a width greater than 3 mm.

Advantageously, the inner faces of the jaws have toothed surfaces with complementary shapes. This arrangement allows satisfactory maintenance of the vein segments in the gripper during the operation.

Advantageously, the jaws are provided at their distal end with one or more claws. These claws allow anchoring of the jaws in the vein wall so as to allow easy removal of the veins.

According to one embodiment of the invention, the means for transmitting the movement include a shaft translatable inside the tubular sheath and two connecting rods each having a first end rotatably mounted on one of the branches and a second end rotatably mounted on one end of the shaft. In this way, these transmission means are particularly simple.

Advantageously, a first jaw is movably mounted relative to a second stationary jaw, around the axis A, and the distal end of the moving shaft is equipped with a connecting rod that is on the one hand movably mounted on said first jaw around a second axis B not combined with the axis A, and on the other hand mounted rotatably on the distal end of the shaft.

According to a second aspect, the invention relates to an assembly including a set of surgical forceps according to the first aspect of the invention, each of said forceps comprising tubular sheaths of different lengths.

BRIEF DESCRIPTION OF THE FIGURES

Other aims and advantages of the invention will appear upon reading the following description, done in reference to the appended drawings, in which.

DETAILED DESCRIPTION OF THE INVENTION

Figure 1:
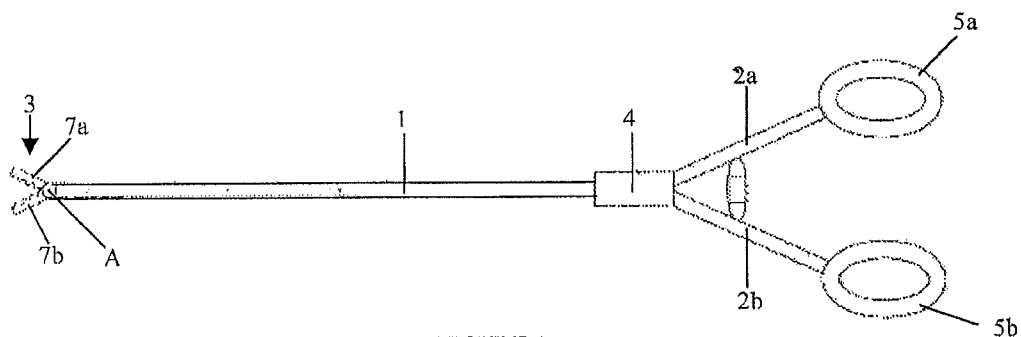
FIG. 1 is a diagrammatic view of a surgical forceps according to the invention.
Figure 2:
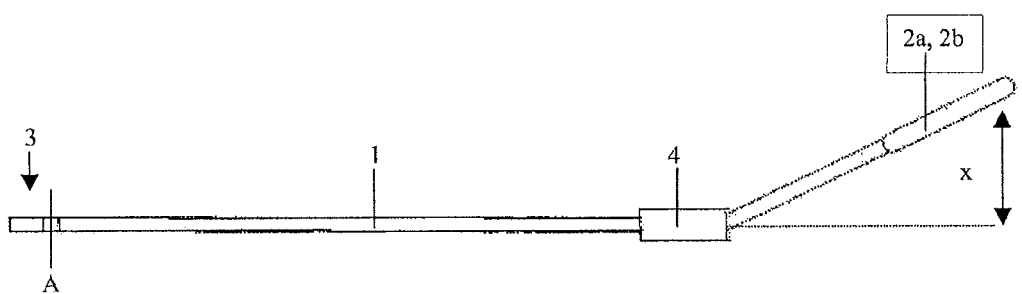
FIG. 2 is a diagrammatic side view of the surgical forceps of FIG. 1.
Figure 4:
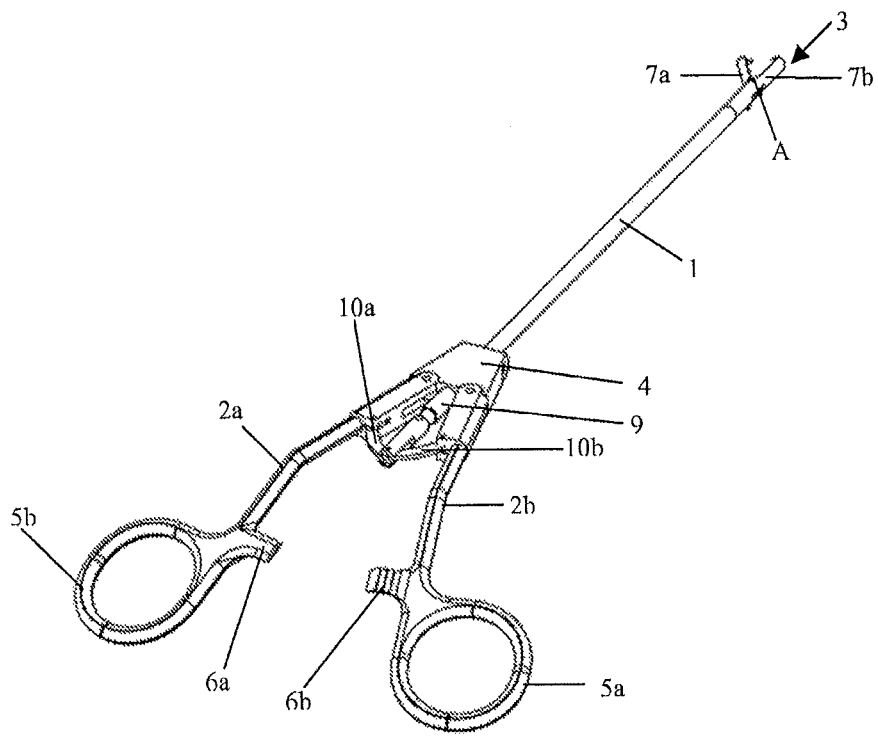
FIG. 4 shows a surgical forceps according to a second embodiment.

A forceps according to the invention, as illustrated in FIGS. 1, 2 and 4, includes a body 1, two maneuvering branches 2a, 2b, and a gripper 3 for gripping veins.

The body includes an articulation plate 4 and a tubular sheath 1 whereof the distal end bears the gripper 3. The tubular sheath 1 has a length comprised between 10 and 25 cm as a function of the desired action radius of the gripper and a section smaller than or equal to 3 mm.

Two maneuvering branches 2a, 2b are mounted, on the articulation plate 4, movable between an open position and a closed position.

Furthermore, the gripper 3 has two jaws 7a, 7b movably mounted relative to one another around an axis A between an open position and a gripping position.

Means, described in detail hereafter, make it possible to transmit the movement from the maneuvering branches 2a, 2b to the gripper 3 through the tubular sheath 1. These means are arranged such that closing the maneuvering branches 2a, 2b causes the jaws 7a, 7b to move toward their gripping position and separating the branches 2a, 2b cause the jaws 7a, 7b to move toward their separated position.

The jaws 7a, 7b extend in a plane, orthogonal to the pivot axis A of said jaws 7a, 7b, which will be called "working plane" hereafter. The tubular sheath 1 also extends in that working plane.

The maneuvering branches 2a, 2b are mounted on the articulation plate 4 and can move relative to one another between an open position and a closed position. In the illustrated embodiments, the two branches 2a, 2b are movably mounted on the articulation plate 4 and pivotably around a same pivot axis. In another embodiment of the invention, it is possible to provide that one of the branches 2a, 2b is stationary relative to the articulation plate 4 while the other branch 2b, 2a is rotatably mounted relative to said stationary branch 2a, 2b.

In order to facilitate maneuvering of the forceps, the rings 5a, 5b are separated relative to the working plane. Preferably, the rings 5a, 5b are separated, relative to said working plane, by a distance x greater than or equal to 1 cm (see FIG. 2). This arrangement makes it possible to improve the ergonomics of the forceps.

In the illustrated embodiments, the rings 5a, 5b extend along the maneuvering plane, which has an angulation of more than 10° relative to the working plane. Preferably, the maneuvering plane is inclined by an angle comprised between 20 and 30° relative to said working plane. The angulation makes it possible to offset the rings 5a, 5b from the plane of the skin, and therefore to facilitate gripping of the rings and manipulation of the rings 5a, 5b relative to an embodiment in which the rings extend in the plane of the tubular sheath 1. In fact, varicose veins being subcutaneous, the forceps is introduced into the skin in a plane substantially parallel to the surface of the skin.

According to a first embodiment shown in FIG. 2, the branches 2a, 2b are substantially longilineal and extend in a maneuvering plane that is inclined relative to the working plane. The pivot axis of the branches 2a, 2b in that case is orthogonal to the maneuvering plane. According to a second embodiment illustrated in FIGS. 4 and 5, the branches 2a, 2b are bent and the pivot axis of the branches 2a, 2b is then orthogonal to the working plane.

Figure 5:
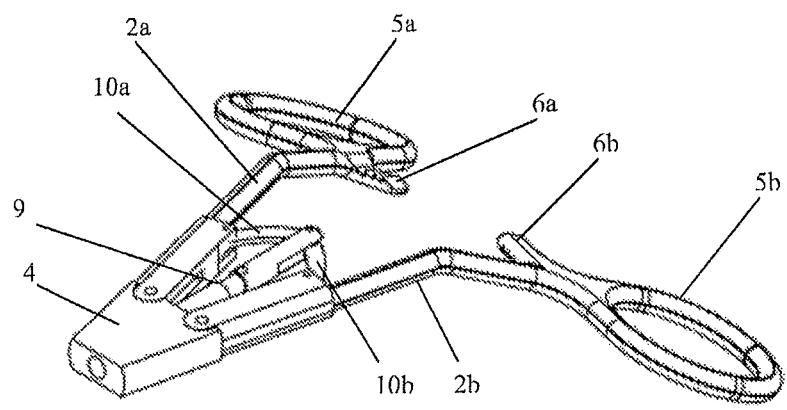
FIG. 5 is a detailed view of the maneuvering portion of the surgical forceps of FIG. 4.

The branches 2a, 2b may also be provided with locking means, shown in FIGS. 4 and 5, assuming the form of lugs 6a, 6b provided with pawls. Each of the branches 2a, 2b bears a lug 6a, 6b oriented toward the lug of the other branch 2b, 2a. The lugs 2a, 2b have two surfaces provided with pawls cooperating one against the other when the branches 2a, 2b are in the closed position. The surfaces perform a rack function and make it possible to keep the jaws closed and under pressure.

Furthermore, the jaws 7a, 7b of the gripper 3 have an interface provided with teeth so as to ensure satisfactory gripping of the vein segments. Advantageously, the interfaces of the jaws have complementary shapes.

Figure 6:
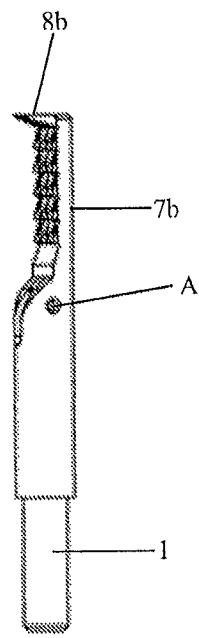
FIG. 6 is a detailed view of the stationary jaw and the distal end of the tubular sheath of the surgical forceps of FIG. 4.
Figure 7:
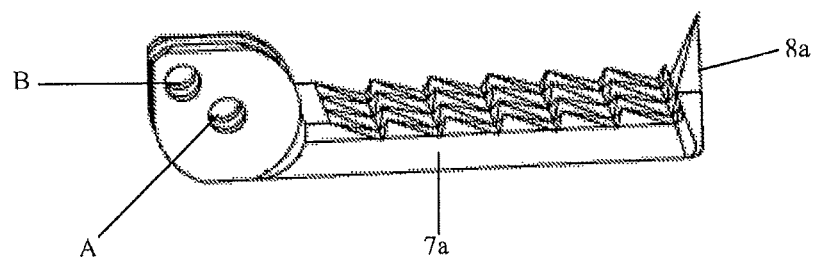
FIG. 7 is a detailed view of the structure of the movable jaw of the forceps of FIG. 4.

FIGS. 6 and 7 show inner surfaces of the jaws 7a, 7b. The inner surface has a plurality of teeth. Preferably, the toothed patterns of the inner surface extend both in the longitudinal and lateral directions of the jaws 7a, 7b.

Furthermore, the distal end of each jaw 7a, 7b is provided with a claw 8a, 8b or hook making it possible to ensure better gripping of the varicose veins. In one advantageous embodiment, one of the jaws 7a, 7b is equipped with two claws 8a, 8b while the other jaw 7a, 7b is equipped with at least one claw 8a, 8b that is inserted between the two claws 8a, 8b of the first jaw 7a, 7b.

Figure 3:
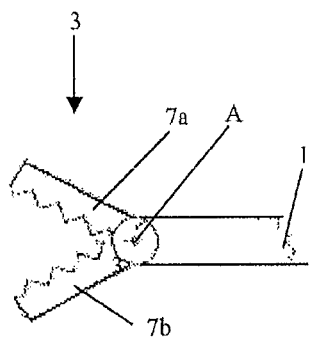
FIG. 3 is a detailed view of the gripper of FIG. 1.

In the embodiment shown in FIGS. 1 and 3, the two jaws 7a, 7b are movably mounted around the pivot axis A.

On the contrary, in the embodiment shown in FIGS. 4, 6 and 7, the gripper 3 has a stationary jaw 7b, shown in FIG. 6, and a moving jaw 7a shown in FIG. 7. The stationary jaw 7b extends substantially in the extension of the tubular sheath 1 and the moving jaw 7a is mounted rotatably, on the stationary jaw 7b, around the axis of rotation A.

In the illustrated embodiment, the movement transmission means include a shaft 9 translatable inside the tubular sheath 1. At a first end of said shaft 9, shown in FIGS. 4 and 5, the transmission means include two connecting rods 10a, 10b. Each of said connecting rods 10a, 10b has a first end rotatably mounted on one of the branches 2a, 2b and a second end rotatably mounted on the first end of the shaft 9. The connecting rods 10a, 10b are arranged such that when the branches 2a, 2b are brought closer together, the shaft 9 slides toward the outside of the sheath 1, and when the branches 2a, 2b are separated from one another, the shaft slides toward the inside of the sheath 1.

The second end of the shaft 9, not shown, is equipped with a connecting rod that is on the one hand hingedly mounted on the shaft 9 and on the other hand hingedly mounted on the moving jaw 7a. This connecting rod is hingedly mounted on the moving jaw 7 around a lever axis B that is not combined with the articulation axis A of the jaw 7a. The lever axis B is determined such that a tractive force on the moving jaw exerted at said lever axis the causes the moving jaw 7a to rotate around the axis A.

The invention is of course not limited to these particular means for transmitting the movement, and any other suitable means may be provided without going beyond the scope of the invention. As an example, it is also possible to provide for transmitting movement using push-pull cables or equivalent means.

Furthermore, the forceps according to the invention may also be equipped with return means, not shown, arranged to return the maneuvering branches 2a, 2b toward their separated position. These return means may in particular be made up of one or more springs.

The phlebectomy forceps is for example made from stainless steel, titanium, carbon, plastic, or a combination of those materials, for example by combining steel and plastic for a single use embodiment. In general, all materials usable in surgery may be considered to manufacture a phlebectomy forceps according to the invention. For forceps intended to be sterilized, materials withstanding autoclave sterilization will be chosen.

The invention also relates to a set of forceps whereof the tubular sheaths have different sizes. In this way, the practitioner can choose the forceps with the most suitable length as a function of the distance between the vein segment to be removed and the incision.

The invention has been described above as an example. One skilled in the art may of course produce different alternative embodiments of the invention without going beyond the scope of the invention.

The invention claimed is:

1. A method of removing varicose veins with surgical forceps, the forceps comprising:
    a body with an articulation plate and an elongate tubular sheath;
    a gripper mounted at a distal end of the tubular sheath having two jaws mounted movably relative to each other around a pivot axis between an open position and a gripping position, the jaws having toothed inner faces;
    two maneuvering branches mounted on the articulation plate and movable relative to each other between an open position and a closed position, each of the branches having a ring for the insertion of a finger, the rings being spaced apart by a distance of at least 1 cm relative to a working plane of the forceps, orthogonal to the pivot axis and in which the jaws extend; and
    a linkage for transmitting the movement of the maneuvering branches to the jaws, via the tubular sheath, said linkage formed to move the jaws to the gripping position when the maneuvering branches are moved towards one another;
    wherein the method comprises:
    inserting a finger in each ring;
    introducing the surgical forceps into a patient's skin in a plane substantially parallel to a surface of the skin such that the working plane is located between the rings and the surface of the skin, wherein the rings are offset from the surface of the skin; and
    moving the maneuvering branches towards one another to move the jaws to the gripping position to grip the varicose veins.

2. The method of claim 1, wherein the rings extend in a maneuvering plane inclined by an angle greater than 10° relative to the working plane.

3. The method of claim 2, wherein the rings extend in the maneuvering plane inclined by an angle between 20 and 30° relative to the working plane.

4. The method of claim 1, wherein the length of the tubular sheath is between 10 and 25 cm.

5. The method of claim 1, wherein the tubular sheath comprises a section smaller than or equal to 3 mm.

6. The method of claim 1, wherein the inner faces of the jaws comprise toothed surfaces having complementary shapes.

7. The method of claim 1, wherein the jaws are provided at their distal end with one or more claws.

8. The method of claim 1, wherein the linkage further comprises a shaft translatable inside the tubular sheath and at least one connecting rod having a first end rotatably mounted on one of the branches and a second end rotatably mounted on one end of the shaft.

9. The method of claim 8, wherein a first of the two jaws is movably mounted relative to a second of the two jaws, which is stationary, around the pivot axis, and a distal end of the shaft is equipped with a connecting rod that is movably mounted on said first jaw around a second axis not identical with the pivot axis, and mounted rotatably on the distal end of the shaft.

10. The method of claim 1, further comprising, prior to the inserting, choosing the forceps from a set of surgical forceps comprising tubular sheaths of different lengths.

* * * * *

UNITED STATES PATENT AND TRADEMARK OFFICE
CERTIFICATE OF CORRECTION

PATENT NO. : 10,251,660 B2
APPLICATION NO. : 15/340802
DATED : April 9, 2019
INVENTOR(S) : Pierre Sarradon Page 1 of 1

It is certified that error appears in the above-identified patent and that said Letters Patent is hereby corrected as shown below:

On the Title Page

Item (54) and in the Specification, Column 1, Line 1, the title should be changed from:
"SURGICAL FORCEPS FOR PHLEBOTOMY"
To:
--SURGICAL FORCEPS FOR PHLEBECTOMY--.

Signed and Sealed this
Tenth Day of December, 2019

Andrei Iancu
*Director of the United States Patent and Trademark Office*